(12) United States Patent
Bonnez (10) Patent No.: US 9,308,237 B2
(45) Date of Patent: Apr. 12, 2016

(54) PAPILLOMAVIRUS VIRUS-LIKE PARTICLE OR CAPSOMERE FORMULATION AND ITS USE AS MICROBICIDE

(75) Inventor: William Bonnez, Rochester, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 13/636,984

(22) PCT Filed: Mar. 22, 2011

(86) PCT No.: PCT/US2011/029308
§ 371 (c)(1),
(2), (4) Date: Dec. 6, 2012

(87) PCT Pub. No.: WO2011/119527
PCT Pub. Date: Sep. 29, 2011

(65) Prior Publication Data
US 2013/0085097 A1 Apr. 4, 2013

Related U.S. Application Data (60) Provisional application No. 61/317,168, filed on Mar. 24, 2010.

(51) Int. Cl.
*A61K 38/16* (2006.01)
*A61K 45/06* (2006.01)

(52) U.S. Cl.
CPC ............... *A61K 38/162* (2013.01); *A61K 45/06* (2013.01); *C12N 2710/20023* (2013.01); *C12N 2710/20032* (2013.01)

(58) Field of Classification Search
None
See application file for complete search history.

(56) References Cited

U.S. PATENT DOCUMENTS 5,595,980 A 1/1997 Brode et al.
2006/0269954 A1* 11/2006 Lowy et al. .................. 435/6

FOREIGN PATENT DOCUMENTS

WO 2004025263 A2 3/2004
WO WO 2009/092113 A2 * 7/2009 ............. A61K 39/00

OTHER PUBLICATIONS

Kreimer et al. Cancer Epidemiol Biomarkers Prev. 14;467-475:2005.*
D'Cruz et al. AAPS PharmSciTech. 2(1);article 5:2001.*
Lu et al. Journal of General Virology. 84;1577-1582:2003.*
Fakruddin et al. Blood. 109(5);1841-1849:2007.*
Kines et al. "The Initial Steps Leading to Papillomavirus Infection Occur on the Basement Membrane Prior to Cell Surface Binding," PNAS 106(48):20458-20463 (2009).
Zhu et al. "Infection of Cells by Varicella Zoster Virus: Inhibition of Viral Entry by Mannose 6-phosphate and Heparin," PNAS 92:3546-3550 (1995).
Alfsen et al. "HIV-a-infected Blood Mononuclear Cells Form an Integrin-and Agrin-dependent Viral Synapse to Induce Efficient HIV-1 Transcytosis across Epithelial Cell Monolayer," Molecular Biology of the Cell 16:4267-4279 (2005).
International Search Report and Written Opinion for PCT/US11/29308, filed Mar. 22, 2011.
Zeitlin et al., "Microbicides for Preventing Transmission of Genital Herpes," Herpes 9(1):4-9 (2002).
Whaley et al., "Preventing Transmission: Plant-Derived Microbicides and Mucosal Vaccines for Reproductive Health," Vaccine 23:1819-1822 (2005).
Zeitlin et al., "Preventing Infectious Disease with Passive Immunization," Microbes and Infection 2:701-708 (2000).
Zeitlin et al., "Tests of BufferGel for Contraception and Prevention of Sexually Transmitted Diseases in Animal Models," Sex. Transmit. Dis. 28(7):417-423 (2001).
de Villiers et al., "Classification of Papillomaviruses," Virol. 324:17-27 (2004).
Sudhakar et al., "Buccal Bioadhesive Drug Delivery—A Promising Option for Orally Less Efficient Drugs," J. Control. Rel. 114:15-40 (2006).
Justin-Temu et al., "Intravaginal Gels as Drug Delivery Systems," J. Wom. Health 13(7):834-845 (2004).
Radomsky et al., "Controlled Vaginal Delivery of Antibodies in the Mouse," Biol. Reprod. 47:133-140 (1992).
Tamura et al., "Interaction of Recombinant Norwalk Virus Particles with the 105-Kilodalton Cellular Binding Protein, a Candidate Receptor Molecule for Virus Attachment," J. Virol. 74(24):11589-11597 (2000).
Lu et al., "Infection Competition against Grouper Nervous Necrosis Virus by Virus-Like Particles Produced in *Escherichia coli*," J. Gen. Birol. 84:1577-1582 (2003).
Culp et al., "Human Papillomaviruses Bind a Basal Extracellular Matrix Component Secreted by Keratinocytes which is Distinct from a Membrane-Associated Receptor," Virol. 347(1):147-159 (2006) (abstract only).
Giroglou et al., "Human Papillomavirus Infection Requires Cell Surface Heparan Sulfate," J. Virol. 75(3):1565-1570 (2001).

(Continued)

*Primary Examiner* — Amber D Steele
*Assistant Examiner* — Schuyler Milton
(74) *Attorney, Agent, or Firm* — LeClairRyan, a Professional Corporation (57) ABSTRACT

Methods and compositions for preventing viral infection are disclosed. Compositions containing papillomavirus VLPs or capsomeres are used, alone or in combination with other agents, as microbicides that substantially block papillomavirus binding receptors on the surface or vicinity of cells in a tissue to be treated with the composition. The invention can be used to inhibit papillomavirus infection or infection by another virus that utilizes the same binding receptors during the infection process.

15 Claims, 1 Drawing Sheet

(56) References Cited

OTHER PUBLICATIONS

Figure 1:
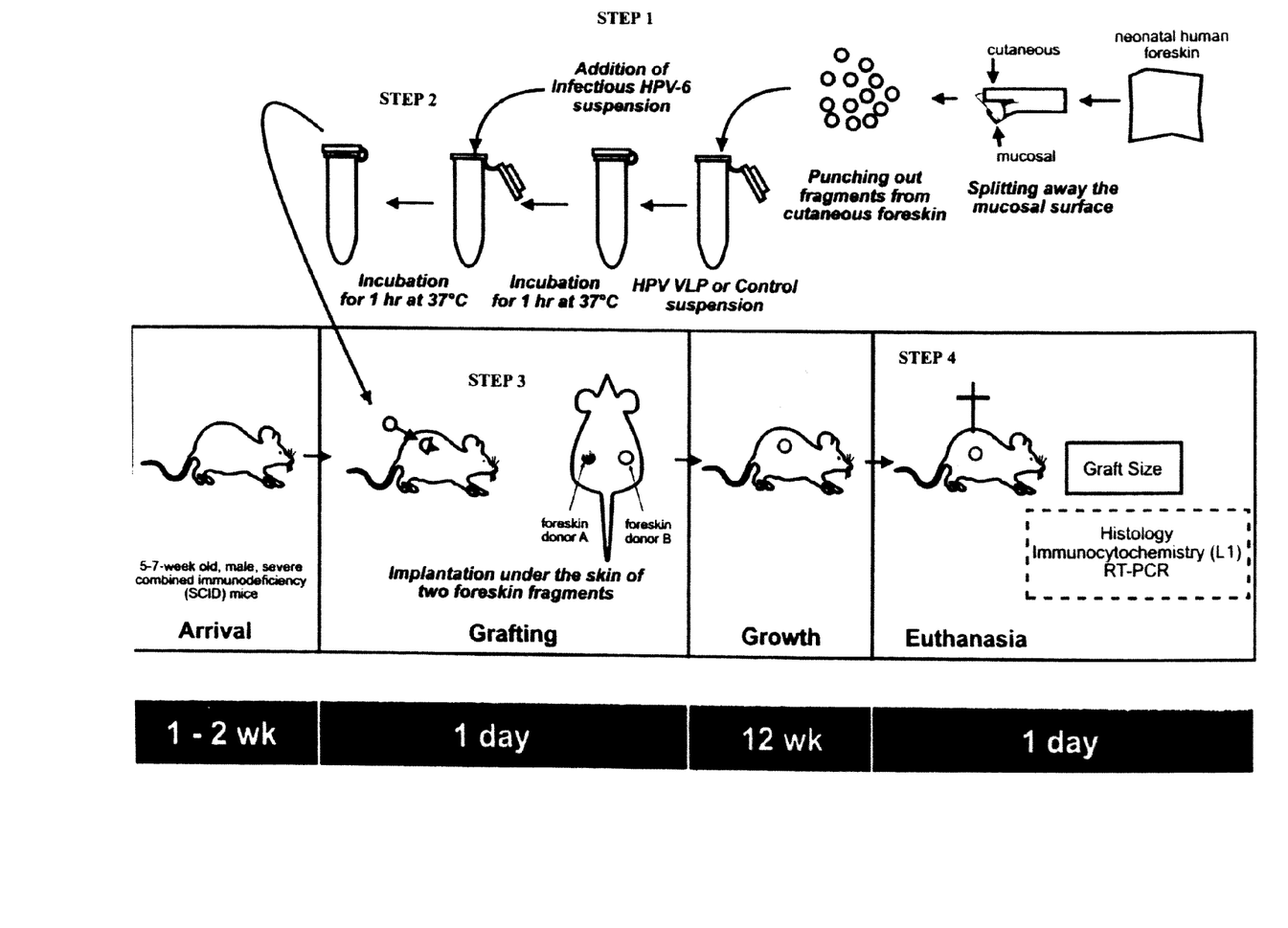

Joyce et al., "The L1 Major Capsid Protein of Human Papillomavirus Type 11 Recombinant Virus-Like Particles Interacts with Heparin and Cell-Surface Glycosaminoglycans on Human Keratinovytes," J. Biol. Chem. 274 (9):5810-5822 (1999).

Zeitlin et al., "Using Monoclonal Antibodies to Prevent Mucosal Transmission of Epidemic Infectious Diseases," Emerg. Infect. Dis. 5(1):54-64 (1999).

Cutts et al., "Human Papillomavirus and HPV Vaccines: A Review," Bulletin W.H.O. 85:719-726 (2007).

Letian et al., "Cellular Receptor Binding and Entry of Human Papillomavirus," Virol. J. 7:2 (2010).

Ohlschlager et al., "Human Papillomavirus Type 16 L1 Capsomeres Induce L1-Specific Cytotoxic T Lymphocytes and Tumor Regression in C57BL/6 Mice," J. Virol. 77(8):4635 (2003).

Bian et al., "Human Papillomavirus Type 16 L1E7 Chimeric Capsomeres Have Prophylactic and Therapeutic Efficacy Against Papillomavirus in Mice," Mol. Cancer Ther. 7:1329-1335 (2008).

Supplementary European Search Report for corresponding EP Application No. 11760019 (mailed Mar. 28, 2014).

European Search Opinion for corresponding EP Application No. 11760019 (mailed Mar. 28, 2014).

* cited by examiner

```
                        SEQUENCE LISTING

<160> NUMBER OF SEQ ID NOS: 9

<210> SEQ ID NO 1
<211> LENGTH: 17
<212> TYPE: DNA
<213> ORGANISM: Artificial
<220> FEATURE:
<223> OTHER INFORMATION: Forward Primer, specific for HPV-6b

<400> SEQUENCE: 1
tgcaaacgcc gcctaga                                                   17

<210> SEQ ID NO 2
<211> LENGTH: 19
<212> TYPE: DNA
<213> ORGANISM: Artificial
<220> FEATURE:
<223> OTHER INFORMATION: Reverse Primer, specific for HPV-6b

<400> SEQUENCE: 2
cacacacaag gcgttgcaa                                                 19

<210> SEQ ID NO 3
<211> LENGTH: 27
<212> TYPE: DNA
<213> ORGANISM: Artificial
<220> FEATURE:
<223> OTHER INFORMATION: Oligonucleotide Probe, specific for HPV-6b

<400> SEQUENCE: 3
aacgagcacg aggagtccaa cagtcac                                        27

<210> SEQ ID NO 4
<211> LENGTH: 20
<212> TYPE: DNA
<213> ORGANISM: Artificial
<220> FEATURE:
<223> OTHER INFORMATION: Forward Primer, specific for GAPDH

<400> SEQUENCE: 4
gcaccgtcaa ggctgagaac                                                20

<210> SEQ ID NO 5
<211> LENGTH: 20
<212> TYPE: DNA
<213> ORGANISM: Artificial
<220> FEATURE:
```

-continued

<223> OTHER INFORMATION: Reverse Primer, specific for GAPDH

<400> SEQUENCE: 5
accatcttcc aggagcgaga                                               20

<210> SEQ ID NO 6
<211> LENGTH: 24
<212> TYPE: DNA
<213> ORGANISM: Artificial
<220> FEATURE:
<223> OTHER INFORMATION: Oligonucleotide Probe, specific for GAPDH

<400> SEQUENCE: 6
agcttgtcat caatggaaat ccca                                          24

<210> SEQ ID NO 7
<211> LENGTH: 18
<212> TYPE: DNA
<213> ORGANISM: Artificial
<220> FEATURE:
<223> OTHER INFORMATION: Forward Primer, specific for beta actin

<400> SEQUENCE: 7
cctggcaccc agcacaat                                                 18

<210> SEQ ID NO 8
<211> LENGTH: 20
<212> TYPE: DNA
<213> ORGANISM: Artificial
<220> FEATURE:
<223> OTHER INFORMATION: Reverse Primer, specific for beta actin

<400> SEQUENCE: 8
gccgatccac acggagtact                                               20

<210> SEQ ID NO 9
<211> LENGTH: 23
<212> TYPE: DNA
<213> ORGANISM: Artificial
<220> FEATURE:
<223> OTHER INFORMATION: Oligonucleotide Probe, specific for beta actin

<400> SEQUENCE: 9
tcaagatcat tgctcctgag cgc                                           23

PAPILLOMAVIRUS VIRUS-LIKE PARTICLE OR CAPSOMERE FORMULATION AND ITS USE AS MICROBICIDE

This application is a national stage application under 35 U.S.C. 371 of PCT Application No. PCT/US2011/029308, filed Mar. 22, 2011, which claims the priority benefit of U.S. Provisional Patent Application Ser. No. 61/317,168, filed Mar. 24, 2010, which is hereby incorporated by reference in its entirety.

FIELD OF THE INVENTION

The present invention relates generally to compositions and methods for the prevention of viral infection.

BACKGROUND OF THE INVENTION

To initiate its life cycle, human papillomavirus ("HPV") needs to enter the basal keratinocyte, the only dividing cell in the normal stratified epithelium, which is able to provide HPV with the necessary DNA replicative molecular machinery it lacks. Viral entry occurs through at least one receptor that was initially believed to be an alpha-6 integrin. However, subsequent work failed to confirm the observation (Evander et al., "Identification of the Alpha6 Integrin as a Candidate Receptor for Papillomaviruses," *J. Virol.* 71(3):2449-2456 (1997) and Giroglou et al., "Human Papillomavirus Infection Requires Cell Surface Heparan Sulfate," *J. Virol.* 75(3):1565-(570 (2001)). Instead, heparan sulfate, a glycosaminoglycan (GAG), is now regarded as the primary receptor for HPV (Giroglou et al., "Human Papillomavirus Infection Requires Cell Surface Heparan Sulfate," *J. Virol.* 75(3):1565-1570 (2001); Joyce et al., "The L1 Major Capsid Protein of Human Papillomavirus Type 11 Recombinant Virus-Like Particles Interacts with Heparin and Cell-Surface Glycosaminoglycans on Human Keratinocytes,"*J. Biol. Chem.* 274(9):5810-5822 (1999); Combita et al., "Gene Transfer Using Human Papillomavirus Pseudovirions Varies According to Virus Genotype and Requires Cell Surface Heparan Sulfate," *FEMS Microbiol. Lett.* 204(1):183-188 (2001); Bousarghin et al., "Positively Charged Sequences of Human Papillomavirus Type 16 Capsid Proteins are Sufficient to Mediate Gene Transfer into Target Cells via the Heparan Sulfate Receptor," *J. Gen. Virol.* 84(Pt 1):157-164 (2003); Drobni et al., "Carboxy-Fluorescein Diacetate, Succinimidyl Ester Labeled Papillomavirus Virus-Like Particles Fluoresce after Internalization and Interact with Heparan Sulfate for Binding and Entry," *Virol.* 310(1):163-172 (2003); Sapp et al., "Structure. Attachment and Entry of Polyoma- and Papillomaviruses," *Virol.* 384(2):400-409 (2009); and Sapp et al., "Viral Entry Mechanisms: Human Papillomavirus and a Long Journey from Extracellular Matrix to the Nucleus," *FEBS J.* 276(24): 7206-7216 (2009)). This initial binding appears to induce a change in the capsid conformation, followed by the binding to a putative second receptor that leads to cellular entry of the virus. Different mechanisms have been proposed for the virus endocytosis, some involving a clathrin- and caveolin-independent mechanism, but others involving a clathrin-coated pit and caveolae mediated fusion to the endosome (Giroglou et al., "Human Papillomavirus Infection Requires Cell Surface Heparan Sulfate," *J. Virol.* 75(3):1565-1570 (2001); Sapp et al., "Structure, Attachment and Entry of Polyoma- and Papillomaviruses," *Virol.* 384(2):400-409 (2009); Sapp et al., "Viral Entry Mechanisms: Human Papillomavirus and a Long Journey from Extracellular Matrix to the Nucleus," *FEBS J.* 276(24):7206-7216 (2009); Selinka et al., "Analysis of the Infectious Entry Pathway of Human Papillomavirus Type 33 Pseudovirions," *Virol.* 299(2):279-287 (2002); and Hindmarsh et al., "Mechanisms Regulating Expression of the HPV 31 L1 and L2 Capsid Proteins and Pseudovirion Entry," *J. Virol.* 4:19 (2007)). The second receptor might be an uncharacterized extracellular matrix component, possibly related to laminin (Culp et al., "Human Papillomaviruses Bind a Basal Extracellular Matrix Component Secreted by Keratinocytes which is Distinct from a Membrane-Associated Receptor," *Virol.* 347(1):147-159 (2006)).

As a GAG, heparan sulfate represents the polysaccharide moiety that is covalently bound to a protein to form a proteoglycan. Syndecan 1, glypican 1, and syndecan 4 are some of the protein moieties to which heparin sulfate binds, and these proteins contribute to different cellular affinities for the HPV capsids (Shafti-Keramat et al., "Different Heparin Sulfate Proteoglycans Serve as Cellular Receptors for Human Papillomaviruses," *J. Virol.* 77(24):13125-13135 (2003)). Heparan sulfate mediates interaction not just with papillomavirus capsids, but also with a wide range of growth factors, morphogens, and receptors. The degree of sulfation (N- and O-sulfation) of heparan sulfate contributes greatly to the various specificities of proteoglycans (Sapp et al., "Structure, Attachment and Entry of Polyoma- and Papillomaviruses," *Virol.* 384(2):400-409 (2009); Sapp et al., "Viral Entry Mechanisms: Human Papillomavirus and a Long Journey from Extracellular Matrix to the Nucleus," *FEBS J.* 276(24): 7206-7216 (2009); Whitelock et al., "Heparan Sulfate: A Complex Polymer Charged with Biological Activity," *Chem. Rev.* 105(7):2745-64 (2005); and Kreuger et al., "Interactions Between Heparan Sulfate and Proteins: The Concept of Specificity," *J. Cell Biol.* 174(3):323-327(2006)). This initial binding of the HPV virions is thought to occur not on the cell surface, but in the extracellular matrix, around the basement membrane. It is not entirely clear if GAGs are essential for HPV virion entry, as heparan sulfate is not required for infection by HPV-31b virions of a skin organotypic culture (Patterson et al., "Human Papillomavirus Type 31b Infection of Human Keratinocytes does not Require Heparan Sulfate," *J. Virol.* 79(11):6838-6847 (2005)). The role of heparans or syndecans in virus cell binding or entry is not limited to papillomavirus; it extends to various herpes viruses, including herpes simplex, adenoviruses and adeno-associated viruses, murine coronavirus, porcine circovirus, dengue, hepatitis C, Sindbis, tick-borne encephalitis, hepatitis B, and HIV (Leistner et al., "Role of Glycosaminoglycans for Binding and Infection of Hepatitis B Virus," *Cell Microbiol.* 10(1): 122-133 (2008); Perabo et al., "Heparan Sulfate Proteoglycan Binding Properties of Adeno-Associated Virus Retargeting Mutants and Consequences for their in vivo Tropism," *J. Virol.* 80(14):7265-7269 (2006); Misinzo et al., "Porcine Circovirus 2 uses Heparan Sulfate and Chondroitin Sulfate B Glycosaminoglycans as Receptors for its Attachment to Host Cells," *J. Virol.* 80(7):3487-3494 (2006); de Haan et al., "Murine Coronavirus with an Extended Host Range uses Heparan Sulfate as an Entry Receptor," *J. Virol.* 79(22): 14451-14456 (2005); Vives et al., "Heparan Sulfate Proteoglycan Mediates the Selective Attachment and Internalization of Serotype 3 Human Adenovirus Dodecahedron," *Virol.* 321(2):332-340 (2004); Spear "Herpes Simplex Virus: Receptors and Ligands for Cell Entry," *Cell Microbiol.* 6(5): 401-410 (2004); Zautner et al., "Heparan Sulfates and Coxsackievirus-Adenovirus Receptor: Each one Mediates Coxsackievirus B3 PD Infection," *J. Virol.* 77(18):10071-10077 (2003); Kroschewski et al., "Role of Heparan Sulfate for Attachment and Entry of Tick-Borne Encephalitis Virus," *Virol.* 308(1):92-100 (2003); Bobardt et al., "Syndecan Captures, Protects, and Transmits HIV to T Lymphocytes," *Immunity* 18(1):27-39 (2003); Shukla et al., "Herpesviruses and Heparan Sulfate: an Intimate Relationship in Aid of Viral Entry," *J. Clin. Invest.* 108(4):503-510 (2001); Goodfellow et al., "Echoviruses Bind Heparan Sulfate at the Cell Surface," *J. Virol.* 75(10):4918-4921 (2001); Birkmann et al., "Cell Surface Heparin Sulfate is a Receptor for Human Herpesvirus 8 and Interacts with Envelope Glycoprotein K8," *J. Virol.* 75(23):11583-11593 (2001); Akula et al., "Human Herpesvirus 8 Interaction with Target Cells Involves Heparan Sulfate," *Virol.* 282(2):245-255 (2001); Dechecchi et al., "Heparan Sulfate Glycosaminoglycans are Involved in Adenovirus Type 5 and 2-Host Cell Interactions," *Virol.* 268(2):382-390 (2000); Byrnes et al., "Binding of Sindbis Virus to Cell Surface Heparan Sulfate," *J. Virol.* 72(9):7349-73456 (1998); Chen et al., "Dengue Virus Infectivity Depends on Envelope Protein Binding to Target Cell Heparan Sulfate," *Nat. Med.* 3(8):866-871(1997); Compton et al., "Initiation of Human Cytomegalovirus Infection Requires Initial Interaction with Cell Surface Heparan Sulfate," *Virol.* 193(2):834-841 (1993); Spear et al., "Heparan Sulfate Glycosaminoglycans as Primary Cell Surface Receptors for Herpes Simplex Virus," *Adv. Exp. Med. Biol.* 313:341-53 (1992); Shieh et al., "Cell Surface Receptors for Herpes Simplex Virus are Heparan Sulfate Proteoglycans," *J. Cell Biol.* 116(5):1273-1281 (1992)).

The binding to the heparan sulfate proteoglycan receptor leads to a change in the conformation of the HPV capsid with shifts in the L1 protein followed by shifts in the L2 protein (Sapp et al., "Structure, Attachment and Entry of Polyoma- and Papillomaviruses," *Virol.* 384(2):400-409 (2009)). This leads to an exposure of the L2 amino-terminus and its cleavage by furin, a serine endoprotease convertase enzyme that cleaves many precursor proteins. Furin may also contribute to the cellular entry of HIV, as well as to the maturation of the influenza and dengue viruses, among others (Nakayama K., "Furin: A Mammalian Subtilisin/Kex2p-like Endoprotease Involved in Processing of a Wide Variety of Precursor Proteins," *Biochem. J.* 327:625-635 (1997); Mukhopadhyay et al., "A Structural Perspective of the Flavivirus Life Cycle," *Nat. Rev. Microbiol.* 3(1):13-22 (2005); and Day et al., "The Role of Furin in Papillomavirus Infection," *Future Microbiol.* 4:1255-62 (2009)). Cell cyclophilins also appear to facilitate this conformation change and binding to a second entry receptor yet to be identified (Sapp et al., "Structure, Attachment and Entry of Polyoma- and Papillomaviruses," *Virol.* 384(2):400-409 (2009); Sapp et al., "Viral Entry Mechanisms: Human Papillomavirus and a Long Journey from Extracellular Matrix to the Nucleus," *FEBS J.* 276(24):7206-7216 (2009); and Bienkowska-Haba et al., "Target Cell Cyclophilins Facilitate Human Papillomavirus Type 16 Infection," *PLoS Pathogens* 5(7):e1000524 (2009)). This binding then initiates the endocytosis of the virus.

It should be pointed out that different investigators have found differences in the viral entry process according to the kind of HPV type studied (Sapp et al., "Structure, Attachment and Entry of Polyoma- and Papillomaviruses," *Virol.* 384(2):400-409 (2009); Sapp et al., "Viral Entry Mechanisms: Human Papillomavirus and a Long Journey from Extracellular Matrix to the Nucleus," *FEBS J.* 276(24):7206-7216 (2009); and Letian et al., "Cellular Receptor Binding and Entry of Human Papillomavirus," *J. Virol.* 7:2 (2010) which are hereby incorporated by reference in their entirety). Papillomaviruses, as most DNA viruses, have evolved slowly, and all infect the same target cell, the basal cell of the stratified epithelium. The epidemiologic uniformity of the infections and diseases caused by genital HPV does not argue for the evolution of different molecular mechanisms of entry. In fact, even HPV types that cause epidermodysplasia verruciformis do infect the genital epithelium (Potocnik et al., "Beta-Papillomaviruses in Anogenital Hairs Plucked from Healthy Individuals," *J. Med. Virol.* 78(12):1673-1678 (2006)). If there are differences in the pathogenesis of the different HPV, they seem to be related to factors intervening after cell entry. Therefore, it is likely, that many, if not the majority of the differences noted in the entry mechanisms of various papillomaviruses, some very closely related like HPV-16 and -31, reflect the various artificial tools that have been used for this research. Native infectious HPV virions are rarely used, because they are difficult to obtain. As a consequence most of the research relies on the use of virus-like particles or pseudovirions. Furthermore, the research also relies on human keratinocyte monolayers or even cells that are not naturally infected by HPV, like mouse cells or epithelia.

Even though effective HPV vaccines are available, different strategies to prevent HPV transmission and infection still need to be addressed. Although a strategy like the use of a microbicide is cumbersome, as the product has to be applied prior to every sexual contact, and costly, several considerations argue for exploring the development of an effective microbicide for HPV, and more broadly, for other sexually transmitted agents. There are other factors that favor development of an effective microbicide for HPV and other sexually transmitted agents. The HPV vaccine coverage of the target population varies by country and is likely to shift, but in the US in 2007, only 25% of the adolescents aged 13 to 17 years had received at least one dose of the HPV vaccine Gardasil (Jain et al., "Vaccination Coverage Among Adolescents Aged 13-17 Years—United States, 2007," *MMWR* 57:1100-1103 (2008)). Many barriers have been identified to increasing HPV vaccine coverage, and their disappearance is unlikely to be complete or sufficient to eliminate the need for additional preventative measures (Humiston et al., "Health Care Provider Attitudes and Practices Regarding Adolescent Immunizations: A Qualitative Study," *Patient Educ. Counsel* 75(1):121-127 (2009)). Among the reasons given by young women for not receiving the vaccine, the most common answers were not being sexually active or not having time to get vaccinated (Jain et al., "Human Papillomavirus (HPV) Awareness and Vaccination Initiation Among Women in the United States, National Immunization Survey—Adult 2007," *Prev. Med.* 48(5):426-431 (2009)). Should the sudden opportunity present to initiate sexual intercourse, these women are likely to seek, at least temporarily, an immediate, private, and easily accessible means of protection, which the vaccine is not. In addition, the HPV vaccine protects the vaccinee, not the sexual partner. A microbicide, in contrast, may be transferred during intercourse from the subject to his/her partner, protecting both individuals from the exchange of an unrecognized HPV infection.

The quest for an effective microbicide against sexually transmitted agents has been recognized to be of high priority by the National Institutes of Health. The only success thus far is a report for a recent study demonstrating that tenofovir in a gel vehicle was able to reduce HIV-1 incidence compared to placebo (Abdool Karim et al., "Effectiveness and Safety of Tenofovir Gel, an Antiretroviral Microbicide, for the Prevention of HIV Infection in Women," *Science* 329:1168-1174 (2010)). Although this is the first report of a potential microbicide for a sexually transmitted disease, the antiviral agent tenofovir most likely acted as an early treatment of HIV-1 infection rather than as a virus entry blocking agent.

The current formulation of Gardasil offers to the HPV-naive individual complete protection against only four types of HPV—types 6, 11, 16, and 18-, and only partial protection against infection or cervical diseases caused by other non-vaccine HPV types (Brown et al., "The Impact of Quadrivalent Human Papillomavirus (HPV; types 6, 11, 16, and 18) L1 Virus-Like Particle Vaccine on Infection and Disease due to Oncogenic Nonvaccine HPV Types in Generally HPV—Naive Women aged 16-26 Years," *J. Infect. Dis.* 199(7):926-935 (2009) and Wheeler et al., "The Impact of Quadrivalent Human Papillomavirus (HPV; types 6, 11, 16, and 18) L1 Virus-Like Particle Vaccine on Infection and Disease due to Oncogenic Nonvaccine HPV Types in Sexually Active Women Aged 16-26 Years," *J. Infect. Dis.* 199(7):936-944 (2009)). Yet, these other non-vaccine types account for the majority of low grade cervical squamous intraepithelial lesions (SIL), and a substantial proportion of the high grade SIL (De Vuyst et al., "Prevalence and Type Distribution of Human Papillomavirus in Carcinoma and Intraepithelial Neoplasia of the Vulva, Vagina and Anus: A Meta-Analysis," *Internat. J. Cancer* 124(7):1626-1636 (2009) and Clifford et al., "Chapter 3: HPV Type-Distribution in Women with and without Cervical Neoplastic Diseases," *Vaccine* 24 Suppl. 3:S26-34 (2006)). The ability to block these infections would be a substantial health benefit. If the receptor(s) of viral entry is common to all genital HPV types, as it appears to be, then it would be desirable to identify a microbicide that could be sufficient to blockade the cellular entry of all HPV types.

It would be desirable, therefore, to provide a composition that is capable of blocking these receptors to prevent PV infection, preferably without risk of jeopardizing the efficacy of any vaccine, i.e., via inducing immune tolerance.

The present invention is directed to overcoming these and other deficiencies in the art.

SUMMARY OF THE INVENTION

A first aspect of the present invention relates to a method of inhibiting virus infection of an individual. This method includes the steps of providing a composition including a plurality of papillomavirus virus-like particles or capsomeres; and contacting a tissue of an individual with the composition under conditions effective substantially to block papillomavirus binding receptors on the surface or vicinity of cells in the tissue, wherein said contacting is effective to inhibit virus infection of the individual.

According to one preferred embodiment, the method is carried out to prevent papillomavirus infection.

According to another preferred embodiment, the method is carried out to prevent infection caused by a different type of virus that also utilizes the same binding receptors for infectivity.

A second aspect of the present invention relates to a composition useful in practicing the first aspect of the invention. The composition includes a contraceptive agent, a plurality of papillomavirus virus-like particles or capsomeres, and a pharmaceutically suitable delivery vehicle.

A third aspect of the present invention relates to a composition useful in practicing the first aspect of the invention. The composition includes a plurality of papillomavirus virus-like particles or capsomeres, and a delivery vehicle, wherein the composition does not contain a separate adjuvant that would contribute to induction of an immune response against the papillomavirus virus-like particles or capsomeres.

A fourth aspect of the present invention relates to a composition useful in practicing the first aspect of the invention. The composition includes a plurality of papillomavirus virus-like particles or capsomeres including an L polypeptide and optionally an L2 polypeptide, which L1 and L2 polypeptides are from a nongenital-specific human papillomavirus or an animal papillomavirus, and a delivery vehicle suitable for application to oral or vaginal mucosa or topical application.

The compositions of the present invention are capable of use as microbicides to prevent or inhibit infection of an individual by papillomavirus or another virus that utilizes a shared papillomavirus binding receptor on the surface or vicinity of cells in the tissue to be treated with the composition. The composition preferably contains a papillomavirus virus-like particle or capsomere that is sufficient to cause receptor blockade, and thereby prevent infection, yet is antigenically distinct of those papillomavirus genotypes that are components of current vaccines and, as such, are unlikely to induce tolerance against the components of those vaccines. Thus, the compositions and methods of the present invention can be used in combination with existing vaccines to prevent the spread of papillomavirus infections as well as infections caused by other viruses.

BRIEF DESCRIPTION OF THE DRAWING

The FIGURE is a schematic showing the HPV-human xenograft severe combined immunodeficiency model as used for the evaluation of HPV VLP as a microbicide against HPV infection.

DETAILED DESCRIPTION OF THE INVENTION

The present invention is directed to methods of inhibiting viral infection of an individual, and compositions suitable for use in these methods of the invention.

This method includes the steps of providing a composition including a plurality of papillomavirus VLPs or capsomeres; and contacting a tissue of an individual with the composition under conditions effective substantially to block papillomavirus binding receptors on the surface or vicinity of cells in the tissue, wherein said contacting is effective to inhibit virus infection of the individual.

The virus infections that can be inhibited in accordance with the present invention include not only papillomavirus infections, but also infections by other infectious agents that utilize the same receptors that papillomaviruses utilize to gain keratinocyte entry (e.g., heparan sulfate and glycosaminoglycans; and laminin). Exemplary non-papillomavirus infectious agents include, without limitation, herpesviridae (e.g., herpes simplex virus 1, herpes simplex virus 2, herpes simplex virus 5, and herpes simplex virus 6), adenovirus, alphavirus (e.g., Ross River virus (RR), Semliki Forest virus (SFV), Sindbis virus (SIN), Venezuelan equine encephalitis virus (VEE)), HIV-1, dengue virus, hepatitis C virus, coronavirus, and/or porcine circovirus.

The individual treated with the compositions of the present invention can be a human or any non-human that is susceptible to infection by one of these infectious agents. Exemplary non-human individuals include, without limitation, non-human primates, horses, dairy cows and cattle, cats, dogs, rabbits, rodents (e.g., rat, mouse, and guinea pig). The individual to be treated can be female or male.

The tissue to be treated in accordance with the present invention can be any tissue that contains one or more papillomavirus binding receptors. As used herein, the term "papillomavirus binding receptor" refers generically to any one or more molecular mechanisms, whether or not it is now known, that facilitate the early steps of papillomavirus infection. As noted above, it is currently believed that one or more of heparan sulfate, glycosaminoglycans, and/or laminin constitute the papillomavirus binding receptor.

As indicated above, the compositions include papillomavirus VLPs or capsomeres. The production of these VLPs or capsomeres via recombinant techniques is well known.

Viruses in the family Papillomaviridae are small, double-stranded, circular DNA tumor viruses. The papillomavirus virion shells consist of the L1 major capsid protein and the L2 minor capsid protein. Expression of L1 protein alone or in combination with L2 protein in eukaryotic or prokaryotic expression systems results in the assembly of VLPs, which are non-infectious and non-replicating, yet morphologically similar to natural virion. Methods for assembly and formation of human papillomavirus VLPs of the present invention are well known in the art (U.S. Pat. No. 6,153,201 to Rose et al.; U.S. Pat. No. 6,165,471 to Rose et al., WO/94/020137 to Rose et al., which are hereby incorporated by reference in their entirety).

As used herein, the papillomavirus VLP or capsomere can be formed using the L1 and, optionally, L2 proteins from any animal papillomavirus, or derivatives or fragments thereof. Thus, the known (or hereafter identified) L1 and L2 sequences of human, bovine, canine, ovine, porcine, deer, feline, rodent, rabbit, etc., papillomaviruses can be employed to prepare the VLPs or capsomeres of the present invention. For a near complete listing of papillomavirus genotypes and their relatedness, see Bernard et al., "Classification of Papillomaviruses (PVs) Based on 189 PV Types and Proposal of Taxonomic Amendments," *Virol.* 401:70-79 (2010), which is hereby incorporated by reference in its entirety.

The L1 protein or polypeptide can be full-length or a polypeptide fragment or derivative thereof that is competent for capsomere or VLP assembly. The L1 sequences are known for substantially all papillomavirus genotypes identified to date. The L2 sequences can also be full length or polypeptide fragments thereof. The L2 sequences are also known for substantially all papillomavirus genotypes identified to date.

The process of preparing VLPs and capsomeres basically involves the preparation of recombinant materials using known procedures, followed by the isolation and purification of these materials via known procedures.

Basically, a nucleic acid construct encoding the L1 or L1/L2 proteins or polypeptide fragments is inserted into any of the many available expression vectors and cell systems using reagents that are well known in the art. Suitable vectors include, but are not limited to, the following viral vectors such as baculovirus lambda vector system gt1 1, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference in its entirety), and any derivatives thereof. The DNA sequences can be cloned into the vector using standard cloning procedures known in the art, including restriction enzyme cleavage and ligation with DNA ligase as described by Sambrook et al., *Molecular Cloning: A Laboratory Manual*, Second Edition, Cold Spring Harbor Press, NY (2001), and Ausubel et al., *Current Protocols in Molecular Biology*, John Wiley & Sons, New York, N.Y. (2008), which are hereby incorporated by reference in their entirety. Recombinant molecules, including plasmids, can be introduced into cells via transformation, particularly transduction, conjugation, mobilization, or electroporation. Once these recombinant plasmids are introduced into unicellular cultures, including prokaryotic organisms and eukaryotic cells, the cells are grown in tissue culture and vectors can be replicated.

For the expression of papillomavirus L1 and L2 proteins or polypeptide fragments, and resulting capsomere and/or VLP assembly, the recombinant vectors produced above are used to infect a host cell. Any number of vector-host combinations can be employed, including yeast vectors and yeast hosts, baculovirus vectors and insect host cells, vaccinia virus vectors and mammalian host cells, or plasmid vectors in *E. coli*.

The capsomeres and/or VLPs of the present invention are preferably formed in Sf-9 insect cells upon expression of the L1 and optionally L2 proteins or polypeptides using recombinant baculovirus. General methods for handling and preparing baculovirus vectors and baculovirus DNA, as well as insect cell culture procedures, are outlined for example in *The Molecular Biology of Baculoviruses*, Doerffer et al., Eds. Springer-Verlag, Berlin, pages 31-49; Kool et al., *Arch. Virol.* 130:1-16 (1993), each of which is incorporated by reference in their entirety.

Regardless of the host-vector system utilized for the recombinant expression of PV capsomeres and/or VLPs, these products can be isolated and purified using known techniques. For example, the purification of the VLPs can be achieved very simply by means of centrifugation in CsCl or sucrose gradients (Kirnbauer et al., "Papillomavirus L1 Major Capsid Protein Self-Assembles into Virus-Like Particles that are Highly Immunogenic," *Proc. Nail. Acad. Sci.* (*USA*) 99:12180-12814 (1992); Kirnbauer et al., "Efficient Self-Assembly of Human Papillomavirus Type 16 L1 and L1-L2 into Virus-Like Particles," *J. Virol.* 67:6929-6936 (1994); Sasagawa et al., "Synthesis and Assembly of Virus-like Particles of Human Papillomaviruses Type 6 and Type 16 in Fission Yeast Schizosaccharomycees pombe," Virology 2016:126-195 (1995); Volpers et al., "Binding and Internalization of Human Papillomavirus Type 33 Virus-Like Particles by Eukaryotic Cells," *J. Virol.* 69:3258-3264 (1995); Zhou et al., "Synthesis and Assembly of Infectious Bovine Papillomavirus Particles in vitro," *J. Gen. Virol.* 74:762-769 (1993); Rose et al., "Expression of Human Papillomavirus Type 11 L1 Protein in Insect Cells: in vivo and in vitro Assembly of Viruslike Particles," *J Virol.* 67(4):1936-1944 (1993); Rose et al., "Serologic Differentiation of Human Papillomavirus (HPV) Types 11, 16, and 18 L1 Virus-Like Particles (VLPs)," *J. Gen. Virol.,* 75:2445-2449 (1994), which are hereby incorporated by reference in their entirety).

Alternatively, for expression in prokaryotes such as *E. coli*, a GST-fusion protein or other suitable chimeric protein can be expressed recombinantly, and thereafter purified and cleaved to afford a self-assembly competent L1 polypeptide that forms capsomeres or VLPs (Chen et al., "Papillomavirus Capsid Protein Expression in *Escherichia coli*: Purification and Assembly of HPV11 and HPV16 L1," *J Mol Biol.* 307: 173-182 (2001), which is hereby incorporated by reference in its entirety). The resulting VLPs or capsomeres can be purified again to separate the structural assemblies from by-products.

Having purified the capsomeres and/or VLPs, these materials can be introduced into compositions of the present invention. Preferably, the VLPs are present in the compositions in an amount that is effective substantially to saturate the PV receptors in a tissue that is to be treated in accordance with the present invention. Thus, effective amounts include an amount ranging from about 1 to about 500 µg of the VLPs or capsomeres, preferably about 25 to about 300 µg, more preferably about 50 to about 200 most preferably about 50 to about 100 µg.

The compositions of the present invention include a pharmaceutically acceptable carrier and an effective amount of the PV VLPs or capsomeres.

Any number of pharmaceutically acceptable carriers can be employed depending upon the intended mode of administration. Suitable modes of administration include, any mode of that allows for delivery of the composition to a tissue comprising the HPV receptors. Exemplary modes of administration include, without limitation, topically to the skin or mucosa, such as those of the nose, throat, gastrointestinal tract, upper airway, oral cavity, anogenital region (including vagina). Preferred routes of administration include as an oral rinse, a vaginal solution, suspension, emulsion, cream or gel, and a topical solution, suspension, emulsion, cream or gel suitable for application to the skin.

Solutions or suspensions can be prepared in water suitably mixed with a mild surfactant that will not disrupt the structure of the VLPs or capsomeres, such as hydroxypropylcellulose. Dispersions can also be prepared in hydroxyethylcellulose, glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers. Under ordinary conditions of storage and use, these preparations contain a preservative to prevent the growth of microorganisms.

An emulsion is a formulation that contains water and oil and is stabilized with an emulsifier. These include lipophilic creams, which are called water-in-oil emulsions, and hydrophilic creams, which are called oil-in-water emulsions. The cream base for water-in-oil emulsions are normally absorption bases such as vaseline, ceresin or lanolin. The bases for oil-in-water emulsions are generally mono-, di- and triglycerides of fatty acids or fatty alcohols with soaps, alkyl sulphates or alkyl polyglycol ethers as emulsifiers.

Other carriers include polymeric vehicles including, without limitation, poly(ethylene-co-vinyl acetate), poly-L-lactide, poly-D-lactide, polyglycolide, poly(lactide-co-glycolide), polyanhydride, polyorthoester, polycaprolactone, polyphosphagene, proteinaceous polymer, polyether, silicone or combinations thereof.

Another suitable type of carrier is a hydrogel matrix. Hydrogels are of special interest in biological environments since they have high water content as is found in body tissue and are highly biocompatible. Hydrogels and natural biological gels have hydrodynamic properties similar to that of cells and tissues. Hydrogels minimize mechanical and frictional irritation to the surrounding tissue because of their soft and compliant nature. Therefore, hydrogels provide a user-friendly delivery vehicle.

Several classes of biodegradable hydrogels have been developed for controlled release of a wide range of bioactive agents. See Kim et al., "Synthesis and Characterization of Dextran-Methacrylate and its Structure Study by SEM," *J. Biomed. Mater. Res.* 49(4):517 (2000); and Park et al., "Biodegradable Hydrogels for Drug Delivery," *Technomic* (1993), which are hereby incorporated by reference in their entirety. These biodegradable hydrogels are synthesized from dextran, a naturally occurring biodegradable, biocompatible, and hydrophilic polysaccharide, and synthetic biodegradable hydrophobic polymers, such as polylactides. Both dextran and synthetic biodegradable polyesters like polyglycolide, polylactide, and their copolymers are FDA approved raw biomaterials that are commercially successful as synthetic, absorbable polymers for biomedical uses, e.g., as wound closure devices. The degradation products of PGA and PLA are natural metabolites and are readily eliminated by the human body. The use of these materials in a delivery vehicle is described, for example, in U.S. Application Publ. No. 20060240071 to Lerner et al., which is hereby incorporated by reference in its entirety. Another exemplary gel formulation is the type employed in the Tenofovir study, which included purified water with edetate disodium, citric acid, glycerin, methylparaben, propylparaben, and hydroxyethylcellulose (HEC) (Abdool Karim et al., "Effectiveness and Safety of Tenofovir Gel, an Antiretroviral Microbicide, for the Prevention of HIV Infection in Women," *Science* 329: 1168-1174 (2010), which is hereby incorporated by reference in its entirety).

A further type of carrier is a buccal bioadhesive formulation, a number of which are known in the art. One exemplary buccal bioadhesive formulation, known as GelClair™, includes water, maltodextrin, propylene glycol, polyvinylpyrrolidone, sodium hyaluronate, potassium sorbate, sodium benzoate, hydroxyethylcellulose, PEG-40 hydrogenated castor oil, disodium edetate, benzalkonium chloride, flavoring, sodium saccharin, and glycyrrhetinic acid.

Yet another form of carrier is a liposomal delivery vehicle, a number of which are known in the art.

The compositions of the present invention may exclude separate adjuvants that would induce a powerful immune response. This is done to minimize the likelihood of inducing immune tolerance against any HPV genotypes that are utilized in commercial HPV vaccines (currently one or more of HPV-6, HPV-11, HPV-16, and HPV-18). In certain embodiments, the compositions of the present invention exclude VLPs or capsomeres derived from these genotypes when the composition is to be administered to humans. VLPs or capsomeres derived from these HPV genotypes would be effective for practicing the present invention in non-human animals, because the immune response generated by these VLPs is genotype specific and these HPV genotypes do not infect non-humans; hence, tolerance simply is not an issue. To the extent that induced tolerance is not a problem when using VLPs or capsomeres of these genotypes in a microbicidal formulation, then in certain embodiments the compositions of the present invention may include VLPs or capsomeres derived from genotypes that are currently employed in human vaccine formulations.

The compositions of the present invention may also include one or more additional therapeutic agents; contraceptive agents; lubricants; buffers, neutralizing agents, agents to adjust pH; agents that preserve efficacy of the VLPs or capsomeres; coloring agents; emollients; emulsifying agents, emulsion stabilizers and viscosity builders; humectants; odorants; preservatives, antioxidants, chemical stabilizers; solvents; thickening, stiffening, and suspending agents; and a balance of water or solvent.

Exemplary therapeutic agents include microbicides effective against other infectious agents, including monoclonal or polyclonal antibody preparations (Zeitlin et al., "Microbicides for Preventing Transmission of Genital Herpes," *Herpes* 9(1):4-9 (2002); Whaley et al., "Preventing Transmission: Plant-derived Microbicides and Mucosal Vaccines for Reproductive Health," *Vaccine* 23:1819-1822 (2005); Zeitlin et al., "Using Monoclonal Antibodies to Prevent Mucosal Transmission of Epidemic Infectious Disease," *Emerging Infectious Diseases* 5(1):54-64 (1999); Zeitlin et al., "Preventing Infectious Disease with Passive Immunization," *Microbes and Infection* 2:701-708 (2000); Zeitlin et al., "Tests of BufferGel for Contraception and Prevention of Sexually Transmitted Diseases in Animal Models," *Sexually Transmitted*

*Diseases* 28(7):417-423 (2001), each of which is hereby incorporated by reference in its entirety.

The contraceptive agent can be any suitable agent, but preferably those that act as spermicides or spermiostatics, those that act to modulate the viscosity of the vaginal mucosal fluid, and those that alter the pH of the vaginal environment to create a spermiostatic environment.

Exemplary spermicides include, without limitation, magnesium chloride, calcium chloride, ferrous sulfate, copper sulfate, ferrous gluconate, and mixtures thereof. The use of these metallic salts as spermiostatic agents, and concentrations effective for spermiostatic efficacy are described in, for example, U.S. Pat. No. 4,959,216 to Daunter; and Shoham et al., "Influence of Different Copper Wires on Human Sperm Penetration Into Bovine Cervical Mucus," *In Vitro Contraception* 36(3):327-34 (1987), which are hereby incorporated by reference in their entirety. The spermicide should not be nonoxynol-9, which has been shown previously to enhance HIV-1 infection.

Exemplary agents to modulate the viscosity of the vaginal mucosal fluid include, without limitation, L-ascorbic acid. It has been shown that L-ascorbic acid, more commonly known as Vitamin C, can act as a reducing agent on the mucopolysaccharides of the cervical mucus. It transfers electrons to the mucopolysaccharides, causing the cervical mucus to change conformation. The open cellular structure that the mucus cells originally have is subsequently closed, thus causing an increase in viscosity. This increased viscosity results in inhibited sperm motility.

Exemplary agents that modulate vaginal pH include, without limitation, poly-amino and polycarboxylic acid mixtures (ampholines) and acid-rich hydrogel materials (e.g., those containing maleic acid).

According to one embodiment, the HEN infection to be inhibited is one which is caused by a genital-specific genotype of human papillomavirus. Exemplary genital-specific genotypes of human papillomavirus include, but are not limited to HPV-6, -11, -16, -18, -30, -31, -33, -34, -35, -39, -60, -62, -43, -64, -65, -51, -52, -53, -54, -56, -58, -59, -61, -62, -66, -67, -68, -69, -70, -71, -74, -81, -85, -86, -87, -89, -90, -91, -92, -101, -102, -103, and -106. Some of the genital-specific genotype human papillomaviruses are associated with cancer, including HPV-16, -18, -31, -33, -35, -39, -45, -51, -52, -56, -58, -59, -66, -67, -68, -73, and -82. In this case, it is preferable that the VLPs or capsomeres are derived from a nongenital-specific genotype of human papillomavirus. These include HPV-1, -2, -3, -4, -7, -10, -22, -28, -29, -36, -37, -38, -41, -48, -49, -60, -63, -67, -72, -76, -77, -80, -88, -92, -93, -94, -98, -95, -96, and -107. VLPs and capsomeres of other HPV genotypes, whether newly discovered or previously known, or even animal papillomavirus types can also be used.

In use, the compositions of the present invention are preferably applied periodically. For example, for application to genital regions, the composition may be applied immediately prior to sexual contact. As another example, medical personnel can apply the composition to their hands immediately prior to examining a patient. Administration can be made to multiple tissue sites using the same or different compositions.

The composition can be used alone or with other barrier protective methods, such as condoms, to prevent the sexual transmission of genital viral infections. This use could be extended and adapted to oro-genital sexual practices that are linked to oropharyngeal cancers.

They can also be used also to coat the birth canal during the delivery by a mother who has cervical, vaginal, or vulvar condylomas to prevent transmission of HPV to the newborn and subsequent development of recurrent respiratory papillomatosis.

It is probable that topical application of HPV VLPs would result in the development of neutralizing antibodies that could be desirable. Even if this were not desirable, it might be possible to alter the neutralizing epitopes of VLPs while retaining the VLP ability to blockade the entry of infectious HPV particles.

EXAMPLES

The Examples set forth below are for illustrative purposes only and are not intended to limit, in any way, the scope of the present invention.

Example 1

Use of HPV Composition to Block HPV-6 Infection in SCID Mouse

The HPV-infected human xenograft severe combined immunodeficiency (SCID) model as used in the proposed experiments is illustrated in the accompanying FIGURE (Bonnez, "The Papillomavirus Human Xenograft Severe Combined Immunodeficient (SCID) Mouse," *In Human Papillomaviruses. Methods and Protocols, Methods Mol. Med.* pp. 203-216 (2005), which is hereby incorporated by reference in its entirety). In this animal model, the target epithelium for genital human papillomavirus infection is, as in natural infections, the foreskin. This model has been shown to recapitulate the macroscopic, microscopic, and molecular features of the native genital HPV infection (Stoler et al., "Infectious Cycle of Human Papillomavirus Type 11 in Human Foreskin Xenografts in Nude Mice," *J. Virol.* 64:3310-3318 (1990); Bonnez, "Murine Models of Human Papillomavirus-Infected Human Xenografts," *Papillomavirus Report* 9:27-38 (1998); and Bonnez, "The HPV Xenograft Severe Combined Immunodeficiency Mouse Model," *Meth. Mol. Med.* 119:203-216 (2005), which are hereby incorporated by reference in their entirety). Discarded foreskins are obtained from routine neonatal circumcisions. The mucosal side of the tissue is ablated with a scalpel blade, and using a biopsy punch, discs of tissue are cut out. The size of the foreskin limits the number of discs, and consequently the size of each experiment.

In the standard model, the discs of foreskin would normally be infected by incubation in a suspension of HPV virions. For the purpose of testing the ability of HPV VLP to block the infection, the discs of foreskin will first be incubated in a suspension of HPV VLP. Three different concentrations of VLP will be evaluated, including a nil concentration that will serve as control, and in separate experiments the L1 VLPs of four different genotypes (HPV-6, HPV-11, HPV-16, and HPV-18). At the end of the incubation, the foreskin discs will be retrieved and placed in a suspension of HPV virions for a second incubation. This step is the challenge exposure that will evaluate how impervious to infection the foreskin has become after exposure to VLPs.

The foreskin discs will then be grafted under the skin of young adult SCID mice, which act as a carrier, allowing the survival of the graft and, if successfully infected by HPV, its proliferation with a histologic and molecular recapitulation of a natural HPV infection. The foreskin grafts can be placed within the mouse skin (orthotopic grafting) or, among other internal locations, under the flank skin (heterotopic grafting). Although the orthotopic grafting is of course closest to a natural infection, as it reproduces human condylomata acuminata on the back of the animal, it does not seem to differ in other significant ways from the heterotopic grafting, which has a distinct advantage over orthotopic grafting. A subcutaneous graft provides a more accurate measurement of the HPV proliferative effect than a cutaneous graft. In a cutaneous (orthotopic) position the graft does not expand much sideways into the mouse epithelium; most of the growth induced by HPV is in height, which is not always easy to measure accurately due to the irregular surface contour of the graft. Moreover, the epithelium desquamates, thus losing some of the proliferation by-product. In contrast, a subcutaneous graft forms an epithelial cyst that grows uniformly along three dimensions, without shedding any cells. Cutaneous and subcutaneous grafts do not differ otherwise.

The foreskin donor has a major influence on the likelihood of infection and resultant graft proliferation. To reduce this source of variability, each mouse is grafted with two grafts coming from two separate foreskin donors. The foreskins of these donors will be prepared separately, and the grafts corresponding to one donor will be placed under the right flank of the animal, and those corresponding to the other donor will be placed under the left flank. Each experiment will be done in quadruplicate, thus involving eight foreskin donors to further control for the foreskin donor effect.

The animal will be monitored for 12 weeks before being euthanized. It is expected that at least nearly all of the implanted grafts will be present at the site of implantation. Their tri-dimensional size will be measured and a geometric mean diameter will serve as the primary endpoint of graft proliferation. The larger the graft, the less likely the HPV infection will have been blocked. The graft will then be split in at least two parts. One part will be fixed in formalin, and processed for histologic and immunocytochemical analysis of the presence of HPV. These will be two of the secondary endpoints. The other part will be snap-frozen in liquid nitrogen, and later processed for quantitative measurement of HPV-6 expression, using quantitative RT-PCR. This will be the third secondary endpoint.

Table 1 below details the specific experimental conditions of the steps shown in the FIGURE. As shown, each experiment uses HPV L1 VLP (henceforth referred as the "Treatment") to block the subsequent infection of the human skin graft by HPV-6. The four experiments will use a different type of VLP: HPV-6, HPV-11, HPV-16, and HPV-18, respectively. Each experiment will be done in quadruplicate. Therefore each experiment will require 48 mice, and 96 grafts. In total, 192 mice will be used for these experiments.

Although, it would be desirable to also vary the genotype of the challenging viral strain beyond HPV-6, the necessary reagents are not available at the moment. Using VLP corresponding to different serotypes should nevertheless provide a strong indication of the genotypes/serotype specificity of the anticipated viral receptor blockade.

TABLE 1

Design of the Main Experiments

| | Step 1: HPV VLP Blocking of Targets | | Step 2: Infectious Challenges | | Step 3: | Step 4: |
|---|---|---|---|---|---|---|
| Experimental Group # | HPV L1 VLP, total volume 200 μL* | Foreskin Incubation Conditions | HPV-6 | Foreskin Incubation Conditions | Mouse Subcutaneous Grafting | Duration of Grafting |
| 1 | Control (diluent alone) | For 60 min at 37° C. | 50 μL[1] | For 60 min at 37° C. | 3 mice | 12 Weeks |
| 2 | 1:100 dilution | | 50 μL | | 3 mice | 12 weeks |
| 3 | 1:10 dilution | | 50 μL | | 3 mice | 12 weeks |
| 4 | 1:1 dilution | | 50 μL | | 3 mice | 12 weeks |

*Two foreskins are used in each replicate experiment, the volumes given here apply to the foreskin fragments coming from one donor. The foreskin fragments of each donor will be incubated separately.

The following materials and methods will be used in carrying out the procedures of this Example:

Viral Stock Replenishment Experiment.

To replenish the stock of HPV-6 used in the experiments described herein, six SCID mice (2 cages) will be grafted with foreskin discs coming from at least two different donors (to minimize the possibility that at least one of the donors will be relatively or totally resistant to HPV-6 infection). Four grafts with be implanted in each animal under the flank skin, two grafts on each side, one rostral, the other caudal. The mice will be maintained for 16 weeks to allow the best proliferation of the infected grafts. The animals will then be sacrificed, the grafts collected, and used for the preparation of a new viral stock.

Animal Species.

Five to seven week old male FOX CHASE C.B-17 SCID (C.B-17/Icr Tac-scidfDF) mice will be used for all experiments. One-hundred ninety-two mice will be used for the main experiment and six mice for the viral stock replenishment experiment, thus a total of 198 mice. No compounds will be administered to the animals, and blood will not be collected.

Preparation of the Foreskin.

Neonatal foreskins from routine circumcision are collected at the nursery of a local hospital, and placed in a transport medium (Dulbecco's Modification of Eagle's Medium [DMEM], penicillin 100 U/mL, streptomycin 100 μg/mL). Two foreskin donors are used in each replicate experiment. Each foreskin is treated in the same way. Foreskins will be collected both the day before and the day of the procedure; however the freshest available tissue on the day of the experiment will be used.

In a Petri dish, the foreskin's occluded side is removed using a scalpel, leaving the exposed skin prepared as a split-thickness graft. The foreskin is punched out using a 4 mm biopsy punch. One fragment is fixed in buffered formalin and serves as control in the histologic and immunocytochemical analyses. Three to four fragments are snap frozen in liquid nitrogen and serve as controls in the RT-PCR assay.

The remaining fragments are processed according to steps 1 and 2 of FIG. 1 and according to Table 1 before being grafted.

Placement of the Grafts.

For grafting, the mouse is anesthetized in an anesthesia chamber with 5% isofluorane per two liters of oxygen, until no corneal or pedal reflexes can be elicited. The animal is removed from the chamber, and the isofluoroane adjusted to 2% per one liter of oxygen for continued administration via nose cone for the duration of the surgical procedure.

The plane of anesthesia is verified by the absence of a palpebral reflex, a normal respiratory rate, the absence of a corneal reflex, of a postural tone, and of withdrawal when notching the ears.

The animal ears are notched for identification. The back skin as well as the left thigh is prepped with a povidone iodine swab. To minimize pain after recovery meloxicam, 2 mg/kg, is administered through the subcutaneous route, with a 27.5 g needle, under a volume less than 100 µL.

A 1 cm vertical incision of the skin is made on the flank with scissors. Through that incision, the subcutis is bluntly dissected with closed scissors caudal to the wound. Foreskin fragments from one donor are assigned to one side of the mouse, those of the other donor to the other side. A single foreskin fragment is inserted in the caudal pocket, epidermis facing the mouse's skin, mucosal side in contact with the musculo-fascial plane (panniculus carnosus) of the mouse. In the viral stock replenishment experiment, two grafts are placed on each flank. The second graft is placed in a pocket created cephalad to the incision. The incision is closed with one or two metal clips. The other side is grafted in the same manner. Clips are removed 7-14 days later.

Euthanasia.

The mice are anesthetized by placing their cage in a ventilated chemical hood. A paper towel saturated with isofluorane is introduced in the cage above the metal grating, and the cover is closed. Once no corneal or pedal reflexes can be elicited the animal is completely removed from its cage, and euthanized by cervical dislocation. Cervical dislocation causes the cessation of respiratory movements, followed by a cardiac arrest. SCID mice are albinos, their retinal reflection is ordinarily pink. The cardiac arrest is associated with the lack of retinal vascular irrigation, causing the eye to assume a gray color. Therefore, the lack of respiration and the change in color of the mouse's eye observed over the approximately 10 minutes that the collection of grafts takes, are both an indication of the animal's death.

Histology and Immunocytochemistry.

The formalin fixed fragments are embedded and sectioned. One hemalum-eosin stain and two unstained poly-L-lysine (PLL)-coated slides are prepared. The hemalum-eosin tissue sections are reviewed for histology. The presence of at least two out of three of the following features: acanthosis, koilocytosis, or parakeratosis is defined as evidence of HPV infection.

For the immunocytochemistry, the PLL-coated slides will be processed using a commercial rabbit antibody directed against the common papillomavirus antigen (Abcam Inc., Cambridge, Mass.) borne by the major capsid protein, and a control rabbit antibody (Jenson et al., "Detection of Papillomavirus Common Antigens in Lesions of Skin and Mucosa," *Clin. Dermatol.* 3(4):56-63 (1985), which is hereby incorporated by reference in its entirety). The immunocytochemistry method has been described elsewhere (see Wilbur et al., "Detection of Infection by Human Papillomavirus in Genital Condylomata. A Comparison Study Using Immunocytochemistry and In Situ Nucleic Acid Hybridization," *Am. J. Clin. Pathol.* 89:505-510 (1988); Bonnez et al., "Antibody Mediated Neutralization of Human Papillomavirus Type 11 (HPV-11) Infection in the Nude Mouse. Detection of HPV-11 mRNAs," *J. Infect. Dis.* 165:376-380 (1992), which are hereby incorporated by reference in their entirety). If a tissue section lacks the tissular elements necessary for the assessment of the presence of HPV, it will be judged as non-interpretable.

The tissue sections will be read by an individual blinded to the Treatment assignments. The presence of HPV as determined by histology and immunocytochemistry will be two of the three secondary endpoints used in the main experiments.

Quantitative RT-PCR and PCR.

The quantitative RT-PCR and PCR will be conducted by the Functional Genomics Center of the University of Rochester. The RT-PCR will measure the magnitude of viral transcription in the samples and will be one of the secondary endpoints in the experiments, along with the histology and immunocytochemistry. The PCR will be used to quantitate the viral stock The following genes will be examined using Taqman chemistry with probes and primers designed to: beta-actin (GenBank X00351), HPV6 (GenBank L41216), and GAPDH (GenBank M33197), each of the Genbank accessions being incorporated herein by reference in its entirety. Probes and primers (Table 2 below) are designed using Primer Express v.1.0 with the following rules added to the default selection criteria provided by the software. Primers for HPV were designed to amplify a majority of viral mRNAs. First, all probes selected contain more C's than G's with no more than four consecutive bases of the same kind. Second, both forward and reverse primers are selected to have at least three of the last five bases be A's or T's preventing clamping at the 3' primer end. The following dye combinations for probe generation are used for detection and data normalization: FAM (reporter—genes of interest), HEX (reporter—normalizer genes) and BHQ1 (non-fluorescent quencher) and ROX (reference). To determine the copy number, a plasmid control, pBluescript KS (Stratagene Inc., La Jolla, Calif.), containing the full genome of the HPV-6a used to infect the graft, will be used. Following probe and primer optimization all cDNA's are diluted 1:100 with 1 µL used for each 10 µL PCR reaction containing: 5 µL of ABI 2× Universal Master Mix, 1.25 µL of each forward and reverse primers (final concentrations ranging from 200-900 nM depending on the primer set), 1 µL of probe (final concentrations ranging from 50-200 nM depending on the probe/primer set) and RNase/DNase free water per reaction. All reactions are performed in triplicate and the experiment replicated three times. Therefore, there are nine individual reactions for each sample being tested. All reactions are run in an ABI 7900 with the following cycle parameters: 1 cycle of 50° C. (2 min) followed by 95° C. (10 min.), 40 cycles of 95° C. (15 sec) followed by 60° C. (1 min). Data is collected at every temperature phase during every cycle. Raw data is analyzed using the Sequence Detection Software (ABI, Foster City Calif.).

TABLE 2

Summary of the Primers and Probes used for the Quantitative RT-PCR and PCR Assays

| Primers/Probes | Nucleotide Sequence (5'-3') | Genomic Nucleotide Position |
|---|---|---|
| HPV 6a | | |
| Forward primer | TGCAAACGCCGCCTAGA (SEQ ID NO: 1) | 3418-3434 |
| Reverse primer | CACACACAAGGCGTTGCAA (SEQ ID NO: 2) | 3464-3482 |
| Probe | (FAM*)AACGAGCACGAGGAGTCCAACAGTCAC(BHQ1*) (SEQ ID NO: 3) | 3436-3462 |
| GAPDH | | |
| Forward primer | GCACCGTCAAGGCTGAGAAC (SEQ ID NO: 4) | 233-252 |
| Reverse primer | ACCATCTTCCAGGAGCGAGA (SEQ ID NO: 5) | 283-302 |
| Probe | (HEX*)AGCTTGTCATCAATGGAAATCCCA(BHQ1) (SEQ ID NO: 6) | 257-280 |
| Beta Actin | | |
| Forward primer | CCTGGCACCCAGCACAAT (SEQ ID NO: 7) | 2717-2734 |
| Reverse primer | GCCGATCCACACGGAGTACT (SEQ ID NO: 8) | 2879-2898 |
| Probe | (HEX)TCAAGATCATTGCTCCTGAGCGC(BHQ1) (SEQ ID NO: 9) | 2852-2877 |

Quantitative PCR will be used to assay the titer of the infecting viral suspension according to the method described by Wang et al., "Robust Production and Passaging of Infectious HPV in Squamous Epithelium of Primary Human Keratinocytes," *Genes Develop.* 23(2):181-194 (2009), which is hereby incorporated by reference in its entirety. The viral suspension is digested with DNase I (Invitrogen), then inactivated by heating for 5 min at 100° C. The viral DNA is freed from the virions by digestion with Proteinase K and phenol/chloroform extractions. Serial dilutions are assayed by quantitative PCR according to the method described for RT-PCR, using as a control the HPV-6a plasmid.

Randomization.

Upon their arrival to the xenograft facility, the animal cages receive a sequential number. This number is used randomly to assign the cages to their Treatment groups. The randomization procedure is carried out with the random number generator of the Minitab software (Minitab, State College, Pa.). The randomization is done the week before the Treatment is to begin.

Analysis of Graft Size.

Graft size is the primary endpoint as it is the closest to the clinical endpoint of interest in the absence of genital wart development. Lack of graft proliferation is indicative of HPV blockade. In a given replicate experiment, each mouse bears on its flanks two grafts, each from one of the two foreskin donors. Therefore, the graft size endpoint is an average, a composite geometric mean diameter (cGMD) of the two grafts borne by the animal defined as:

$$cGMD = \sqrt[3]{(length \times width \times height)_{left\ side} + (length \times width \times height)_{right\ side}}$$

In case one of the two grafts is missing at autopsy, the GMD of the remaining graft will be used.

cGMD, the dependent variable, will be analyzed by a 2-way ANOVA, the two factors being Treatment and replicate (to control for the foreskin donor effect), each treated as fixed. The statistical power of the protocol design, which includes four Treatment levels (including the control), four replicate levels, and three animals per cell can be expressed as an effect size. The effect size being the difference between the largest and smallest mean cGMDs, divided by the within-cell standard deviation (J. COHEN, STATISTICAL POWER ANALYSIS FOR THE BEHAVIORAL SCIENCES (Lawrence Erlbaum Assoc. 1988), which is hereby incorporated by reference in its entirety). For alpha=0.05, and a power of (1-beta)=0.80, the design is powered to detect an effect size, delta, of 0.59, which is large and should leave no doubt about the biological significance of the effect (J. COHEN, STATISTICAL POWER ANALYSIS FOR THE BEHAVIORAL SCIENCES (Lawrence Erlbaum Assoc. 1988), which is hereby incorporated by reference in its entirety).

For a difference among Treatment groups, an analysis for linear or quadratic trend will be conducted across the different VLP concentrations. As part of the exploratory (post-hoc) analysis, pairwise comparisons may be done between the Treatment groups (Spjotvoll & Stoline test, an adaptation of the Tukey 'honestly significant difference' test) or compare the control group to the VLP blocked groups together (Dunnett's test). The four experiments corresponding to the VLPs of each of the four HPV types will be analyzed separately, by analyzing whether there was blockade of HPV infection by heterotypic VLPs. No attempt will be made to analyze statistically if the VLP of one HPV type blocked better than another, because the experiments do not share the same foreskin donors, a major factor in the magnitude of the graft proliferation.

Analysis of Histology and Immunocytochemistry.

The results of histology, presence or absence of HPV, are analyzed by exact logistic regression. The two independent variables are Treatment and foreskin donor. The Treatment variable is treated as qualitative. Because foreskin donor has 8 non-ordered levels, it is made binary by the use of dummy variables. A Treatment-foreskin donor interaction term is not incorporated in the initial model. Should the model lack goodness-of-fit, the Treatment effect will be analyzed by the Fisher-Freeman-Halton test without adjusting for the Foreskin Donor variable. As with graft size, it will be determined whether VLPs block the histologic or immunologic manifestations of an HPV infection, and whether there is a dose-response effect. The second question answered will be whether the blockade is preventative with each of the VLP HPV types.

Analysis of Quantitative RT-PCR. The results of the quantitative RT-PCR will be analyzed by the same methods used for the graft size analysis. Namely the HPV RNA copy number of the two grafts implanted in a mouse will be averaged, and each experiment will be analyzed by a 2-way ANOVA, the two factors being Treatment and replicate (to control for the foreskin donor effect), each treated as fixed.

In all statistical analyses two-sided p values equal or less than 0.05 are considered significant.

Summary.

It is believed that a clear difference will be demonstrated between the control group and one or more of the treatment groups. There may or may not be a difference in the cGMD among the different treatment groups. If such a difference exists, then it is expected that the differences between the treatment groups will reflect an inverse relationship between the concentration of the blocking HPV VLP and graft size.

Although the invention has been described in detail for the purpose of illustration, it is understood that such detail is solely for that purpose, and variations can be made therein by those skilled in the art without departing from the spirit and scope of the invention which is defined in the following claims. Further, even though specific combinations may not be explicitly recited herein, it is to be understood by persons of skill in the art that such combinations of features are intended to be encompassed by the present disclosure for the recited products and methods.

What is claimed is:

1. A method of temporarily inhibiting virus infection incidental to sexual activity of an individual, the method comprising:
providing a microbicide composition comprising a plurality of non-infectious papillomavirus virus-like particles or capsomeres; and
contacting, via topical administration, mucosa or skin tissue of an individual with the composition to block papillomavirus binding receptors on the surface or vicinity of cells in the contacted mucosa or skin,
wherein said contacting is carried out prior to each sexual activity that poses a threat of exposure of the contacted mucosa or skin to a virus, and said contacting is effective temporarily to inhibit virus infection or virus-induced tissue proliferation of contacted mucosa or skin.

2. The method according to claim 1, wherein the virus infection or virus-induced tissue proliferation inhibited by said contacting is a papillomavirus infection or papillomavirus-induced tissue proliferation.

3. The method according to claim 2, wherein the individual is a human and the inhibited papillomavirus infection or virus-induced tissue proliferation is by a human papillomavirus.

4. The method according to claim 3, wherein the papillomavirus virus-like particles or capsomeres comprise an L1 polypeptide and optionally an L2 polypeptide, which L1 and L2 polypeptides are from a non-human papillomavirus.

5. The method according to claim 3, wherein the inhibited human papillomavirus infection or virus-induced tissue proliferation is one which is caused by a genital-specific genotype of human papillomavirus.

6. The method according to claim 5, wherein the papillomavirus virus-like particles or capsomeres comprise an L1 polypeptide and optionally an L2 polypeptide, which L1 and L2 polypeptides are from a nongenital-specific genotype of human papillomavirus.

7. The method according to claim 6, wherein the L1 and L2 polypeptides are from HPV-1, -2, -3, -4, -7, -10, -27, -28, -29, -36, -37, -38, -41, -48, -49, -60, -63, -65, -72, -76, -77, -80, -88, -92, -93, -94, -95, -96, or -107.

8. The method according to claim 5, wherein the genital-specific genotype of human papillomavirus is HPV-6, -11, -16, -18, -30, -31, -33, -34, -35, -39, -40, -42, -43, -44, -45, -51, -52, -53, -54, -56, -58, -59, -61, -62, -66, -67, -68, -69, -70, -71, -74, -81, -83, -84, -85, -86, -87, -89, -90, -91, -97, -101, -102, -103, or -106.

9. The method according to claim 2, wherein the contacted tissue is an ano-genital tissue or an oral tissue.

10. The method according to claim 1, wherein the virus infection inhibited by said contacting is an infection caused by a virus selected from the group consisting of herpes virus, an adenovirus, an alphavirus, HIV-1, dengue virus, hepatitis C virus, a coronavirus, and porcine circovirus.

11. The method according to claim 1, wherein the individual is a non-human animal.

12. The method according to claim 1, wherein the composition also includes a contraceptive agent that is not nonoxynol-9.

13. The method according to claim 1, wherein the composition does not contain an adjuvant that would contribute to induction of an immune response against the papillomavirus virus-like particles or capsomeres.

14. The method, according to claim 1, wherein said contacting is carried out immediately prior to the sexual activity.

15. The method according to claim 1, wherein the method consists of said providing and said contacting.

* * * * *